US009535086B2

(12) United States Patent
Beyeler et al.

(10) Patent No.: US 9,535,086 B2
(45) Date of Patent: Jan. 3, 2017

(54) INTERFACE OF A MICROFABRICATED SCANNING FORCE SENSOR FOR COMBINED FORCE AND POSITION SENSING

(71) Applicant: FEMTOTOOLS AG, Buchs (CH)

(72) Inventors: Felix Beyeler, Regensdorf (CH); Simon Muntwyler, Zurich (CH)

(73) Assignee: FemtoTools AG, Buchs (CH)

( * ) Notice: Subject to any disclaimer, the term of this patent is extended or adjusted under 35 U.S.C. 154(b) by 0 days.

(21) Appl. No.: 14/742,105

(22) Filed: Jun. 17, 2015

(65) Prior Publication Data

US 2015/0369839 A1 Dec. 24, 2015

(30) Foreign Application Priority Data

Jun. 24, 2014 (EP) ..................... 14173713

(51) Int. Cl.
| | | |
|---|---|---|
| *G01Q 20/00* | (2010.01) | |
| *B81C 99/00* | (2010.01) | |
| *G01Q 20/04* | (2010.01) | |
| *G01Q 60/36* | (2010.01) | |
| *G01N 3/42* | (2006.01) | |
| *G01L 1/14* | (2006.01) | |
| *G01L 5/00* | (2006.01) | |
| *G01Q 10/04* | (2010.01) | |

(52) U.S. Cl.
CPC ............ *G01Q 20/00* (2013.01); *B81C 99/005* (2013.01); *G01L 1/148* (2013.01); *G01L 5/0038* (2013.01); *G01N 3/42* (2013.01); *G01Q 10/045* (2013.01); *G01Q 20/04* (2013.01); *G01Q 60/366* (2013.01); *G01N 2203/0286* (2013.01)

(58) Field of Classification Search
CPC ...... B81C 99/005; G01L 1/148; G01L 5/0038; G01N 3/42; G01Q 10/045; G01Q 20/00; G01Q 20/04; G01Q 60/366
See application file for complete search history.

(56) References Cited

U.S. PATENT DOCUMENTS

| | | | |
|---|---|---|---|
| 5,801,472 A | * | 9/1998 | Wada .................. G11B 9/14 310/309 |
| 7,654,159 B2 | | 2/2010 | Enoksson et al. |
| | | (Continued) | |

FOREIGN PATENT DOCUMENTS

CH WO 2010112242 A1 * 10/2010 ............. G01L 1/148

OTHER PUBLICATIONS

Zhu et al., "A microelectromechanical load sensor for in situ electron and x-ray microscopy tensile testing of nano-structures" Applied Physics Letters 86, 013506 (2005).

(Continued)

*Primary Examiner* — Wyatt Stoffa
(74) *Attorney, Agent, or Firm* — Laurence A. Greenberg; Werner H. Stemer; Ralph E. Locher

(57) ABSTRACT

A micro fabricated sensor for micro-mechanical and nano-mechanical testing and nano-indentation. The sensor includes a force sensing capacitive comb drive for the sensing of a force applied to a sample, a position sensing capacitive comb drive for the sensing of the position of a sample and a micro fabricated actuator to apply a load to the sample. All the sensor components mentioned above are monolithically integrated on the same silicon MEMS chip.

10 Claims, 3 Drawing Sheets

(56) References Cited

U.S. PATENT DOCUMENTS

| | | | |
|---|---|---|---|
| 8,161,803 B2 | 4/2012 | Oh et al. | |
| 2007/0180924 A1 | 8/2007 | Warren et al. | |
| 2008/0315092 A1* | 12/2008 | Kley | G01N 23/225 250/307 |
| 2009/0007668 A1* | 1/2009 | Beyeler | G01P 15/0802 73/514.32 |
| 2009/0322365 A1* | 12/2009 | Garmire | B81C 99/005 324/750.3 |
| 2010/0095780 A1* | 4/2010 | Oh | B81C 99/005 73/774 |
| 2010/0132441 A1* | 6/2010 | Oh | G01N 3/42 73/82 |
| 2011/0265559 A1* | 11/2011 | Oh | B82Y 35/00 73/81 |
| 2012/0297897 A1* | 11/2012 | Espinosa | G01N 3/08 73/862.626 |
| 2013/0037512 A1* | 2/2013 | Sun | B81C 99/002 216/13 |
| 2013/0098144 A1* | 4/2013 | Oh | G01N 3/42 73/81 |
| 2013/0098145 A1* | 4/2013 | Oh | G01N 3/42 73/81 |
| 2015/0177272 A1* | 6/2015 | Clark | G01P 15/097 850/5 |

OTHER PUBLICATIONS

Desai et al., "A novel MEMS nano tribometer for dynamic testing in-situ in SEM and TEM", Tribology Letters, vol. 18, No. 1, Jan. 2005, 13.

Nafari et al., "A micromachined nanoidentation force sensor", Sensors and Actuators A 123-124, (2005) 44-49.

Sun et al., "A bulk micro fabricated multi-axis capacitive cellular force sensor using transverse comb drives" Journal of Micromechanics and Microengineering 12, (2002), 832-840.

Sun et al., "A Novel Dual-Axis Electrostatic Microactuation System for Micromanipulation", Proceedings of the 2002 IEE/RSJ Intl. Conference on Intelligent Robots and Systems EPFL, Lausanne, Switzerland Oct. 2002.

Espinosa, H.D., et al.: "Design and Operation of a MEMS-Based Material Testing System for Nanomechanical Characterization," Journal of Microelectromechanical Systems, IEEE Service Center, US, vol. 16, No. 5, Oct. 31, 2007, pp. 1219-1231, XP011193319.

* cited by examiner

INTERFACE OF A MICROFABRICATED SCANNING FORCE SENSOR FOR COMBINED FORCE AND POSITION SENSING

CROSS-REFERENCE TO RELATED APPLICATION

This application claims the priority, under 35 U.S.C. §119, of European application EP 14 173 713.0, filed Jun. 24, 2014; the prior application is herewith incorporated by reference in its entirety.

BACKGROUND OF THE INVENTION

Field of the Invention

The present invention relates to a scanning force sensor.

The knowledge of small forces is crucial for the understanding of physical and biological processes. The evolution of micro-systems and nano-systems has made measurement of very small forces possible and feasible. Several fields of research as well as multiple industrial sectors require solutions for small force metrology. The ongoing trend towards miniaturization requires the development of new tools and quality testing equipment. Also, the in-depth mechanical characterization of micron-sized biological samples such as biological cells leads to a better understanding of biological process, which is fundamental for the development of new diagnostic processes and treatments. The largest application areas where the micro force sensing technology is currently applied are: microsystems and nanosystems development, material science and testing, quality control of miniaturized systems, and biological/biomedical research.

In almost all applications force-displacement information is measured, the force signal alone does not allow detailed mechanical characterization of a micron sized sample. By combining micro force sensing with accurate displacement sensing, measurement tasks like compression (nano-indentation) or tensile tests can be performed.

Several research groups and companies have published micro fabricated force sensors based on different measurements principles such as piezoresistive, optical or capacitive sensing. Most of these sensors have to be mounted onto a high resolution micromanipulator (e.g. a piezoelectrical scanner) for the application of the force to the sample. This micromanipulator requires encoders to measure the position of the force sensor. The encoder signal in combination with the force sensor signal can then be used to obtain the force-deformation information (or stress-strain information respectively) which is characteristic for the sample to be tested. Deformations that occur in the force sensor itself have to be compensated for or must be actively controlled to avoid measurement errors.

Currently, many micromechanical tests are conducted using atomic force microscopes (AFM). However, AFM cantilevers are not well suited for mechanical testing such as compression testing or indentation due to the tilting of the AFM cantilever during the load application.

State-of-the art measurements systems such as tensile/compression testers or nano-indenters normally include the three components: a force sensor, a position encoder and a micromanipulator.

These components are usually large and feature a complex build-up. Combining these components on a single micro-electromechanical system (MEMS) chip reduces the size down to a few mm. This is a great advantage in measurement setups where space is limited such as optical microscope tables or scanning electron microscope chambers. Additionally, by integrating the force sensing, position sensing and actuation mechanism on a MEMS chip, the cost of the system is significantly reduced.

Several MEMS transducers exist that have been used for micro-mechanical and nano-mechanical testing such as tensile testing and nano-indentation [1]-[5]. Some of these transducers are using the principle of capacitive sensing [3][8]. These sensors can measure either a deflection or a force but not both, which does not directly allow the measurement of the force-deformation curve or stress-strain information respectively.

The designs described in [6]-[8] are closest to the invention described in this document. However, there is a number of fundamental differences to these designs in [6], -[8]. In documents [6] and [7] a single differential comb drive is used for position sensing. Only one movable body is used. There is no comb drive used to directly measure force. Therefore, this design cannot be used for direct force-position measurements without mathematical models that are taking the actuation signal into account. Document [8] describes a two-axis transducer for measuring positions in two directions using multiple comb drives. One movable body is used only. The design in [8] cannot be used to directly measure force. A direct force-position measurement is not possible. Simultaneous two-channel force-position readout is improving the accuracy of the measurement since no model-based calculation of the force is required, making use of inaccurate assumptions. Additionally, [6]-[8] do not include electro thermal actuation mechanisms.

SUMMARY OF THE INVENTION

It is accordingly an object of the invention to provide a design and an interface of a micro fabricated scanning force sensor for combined force and position sensing that overcomes the above-mentioned disadvantages of the prior art devices of this general type.

With the foregoing and other objects in view there is provided, in accordance with the invention, a micro-electromechanical system scanning force sensor for a simultaneous measurement of a force and a deformation of a sample. The scanning force sensor contains a position sensing capacitive comb drive for measuring the deformation of the sample, a force sensing capacitive comb drive for measuring the force applied to the sample, and a micro-actuator for applying a mechanical load onto the sample.

In accordance with an added embodiment of the invention, the micro-actuator is an electrostatic micro-actuator or an electro-thermal micro-actuator.

In accordance with a further feature of the invention, there is provided outer flexures, inner flexures, an outer movable body suspended by multiple ones of the outer flexures and an inner movable body suspended by multiple ones of the inner flexures.

In accordance with an additional feature of the invention, there is further provided a sensor probe connected to the inner movable body.

In accordance with another feature of the invention, there is further provided a force sensor capacitive interface, and a position sensor capacitive interface. The force sensing capacitive comb drive and the position sensing comb drive generate two independent capacitive output signals that are interfaced by the force sensor capacitive interface and the position sensor capacitive interface.

In accordance with a further added feature of the invention, there is further provided a fixed body. The electrostatic micro-actuator or the electro-thermal micro-actuator are mechanically connected to the outer movable body to generate a relative motion between the outer movable body and the fixed body.

In accordance with another additional feature of the invention, the position sensing capacitive comb drive measures a relative motion between the inner movable body and the fixed body. Furthermore, the force sensing capacitive comb drive measures a relative motion between the inner movable body and the outer movable body.

In accordance with yet another feature of the invention, there is provided a cooling rip. The electro-thermal micro-actuator is connected to the outer movable body by the cooling rip.

In another embodiment of the invention, the electro-thermal micro-actuator has a v-shaped geometrical amplification mechanism to increase a scanning range of the scanning force sensor.

In accordance with a further embodiment of the invention, there is further provided a support selected from the group consisting of a printed circuit board and a chip carrier. A sensor probe is electrically connected to the printed circuit board or to the chip carrier through at least one of the outer flexures and at least one of the inner flexures.

In accordance with a concomitant feature of the invention, there is further provided a multi-channel capacitive interface electronics integrated circuit. The components of the scanning force sensor are mounted on the printed circuit board or on the chip carrier including the multi-channel capacitive interface electronics integrated circuit.

Other features which are considered as characteristic for the invention are set forth in the appended claims.

Although the invention is illustrated and described herein as embodied in a design and an interface of a micro fabricated scanning force sensor for combined force and position sensing, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
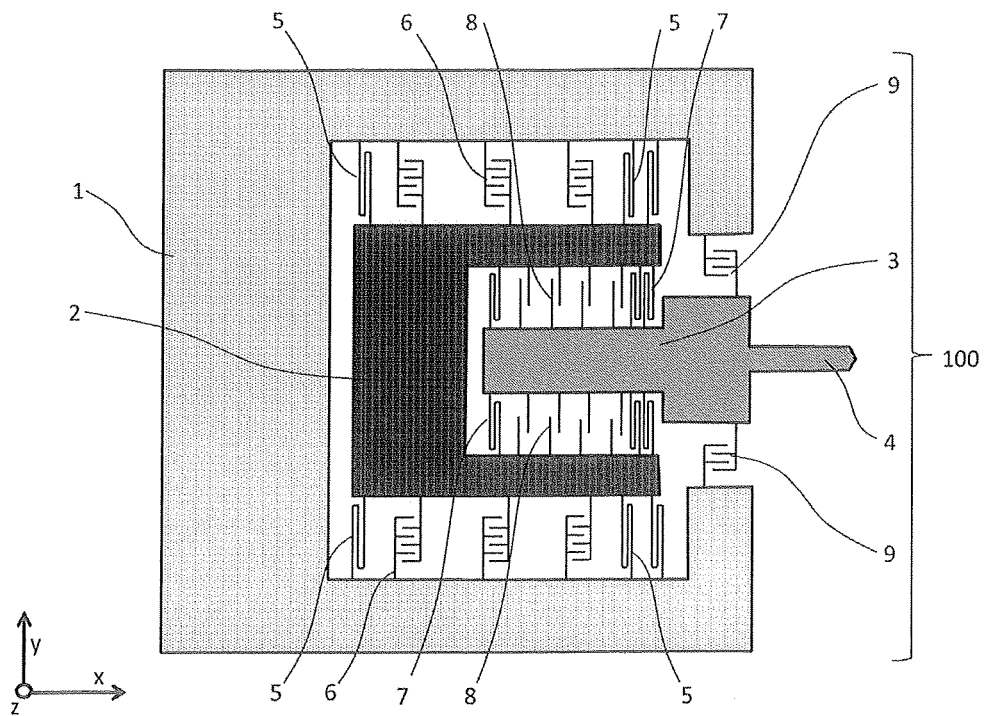
FIG. 1 is an illustration of a scanning MEMS force sensor chip with electrostatic actuation according to the invention.

Referring now to the figures of the drawings in detail and first, particularly to FIG. 1 thereof, there is shown a MEMS based scanning force sensor 100 for micro-mechanical and nano-mechanical testing. The sensor includes a force sensing capacitive comb drive for the sensing of a force applied to a sample, a position sensing capacitive comb drive 9 sensing of the deformation of the sensor probe tip (and therefore the deformation of the sample) and a micro fabricated electrostatic actuator 6 or a micro fabricated electro-thermal actuator 7 for applying the mechanical load (force and deformation) onto the sample. All the sensor components are monolithically integrated on the same silicon MEMS chip as shown in FIG. 1.

FIG. 1 shows the build-up of the scanning force sensor 100. The scanning force sensor 100 consists of the following parts:

a fixed body 1;
an outer movable body 2;
an inner movable body 3;
a sensor probe 4;
multiple outer flexures 5 connecting the outer movable body 2 to the fixed body 1;
multiple inner flexures 7 connecting the inner movable body 3 to the outer movable body 2;
a differential position sensing capacitive comb drive 9 for measuring the position of the inner movable body 3 relative to the fixed body 1;
a differential force sensing capacitive comb drive 8 for measuring the force applied to the sensor probe 4 by measuring a deflection of the inner movable body 3 relative to the outer movable body 1; and
a micro fabricated electrostatic actuator 6 or an electro-thermal actuator 7 which is driving the outer movable body 2.

All parts are located on the same canning force sensor 100 chip. The material of this chip is highly doped (conductive) silicon with a resistivity below 0.1 Ohm-cm. The sensor chip is fabricated by deep reactive ion etching (DRIE) of a silicon-on-insulator (SOI) wafer.

The fixed body 1 is non-movable and attached to the substrate such as a chip carrier or a printed circuit board (PCB). The outer movable body 2 is elastically suspended by multiple outer flexures 5 such that it can deflect in the x-direction. The stiffness of the outer suspension in the x-direction is given by the equation:

$$k_o = n_{fo} \frac{E t w_o}{l_o^3}.$$

Where $k_o$ is a spring constant of the outer suspension, $n_{fo}$ is the number of outer flexures 5 in a parallel configuration, E is the Youngs Modulus of silicon, t is a wafer thickness (thickness in z-direction), $w_o$ is a width of the outer flexures 5 and $l_o$ is a length of the outer flexures 5. The restoring force Fro created by the outer flexures 5 at a deflection x is given by the equation:

$$F_{ro} = k_o x = n_{fo} \frac{E t w_o}{l_o^3} x.$$

The outer movable body 2 is u-shaped such that the inner movable body 3 can be located inside this "u". The inner movable body 3 is elastically suspended by multiple inner flexures 7 such that it can deflect in the x-direction. The stiffness of the inner flexures 7 in the x-direction is given by $$k_i = n_{fi} \frac{Etw_i}{l_i^3}$$

where $k_i$ is the spring constant of the inner suspension, E is the Youngs Modulus of silicon, t is the wafer thickness (thickness in z-direction), $w_i$ is the width of the inner flexures 7 and $l_i$ is the length of the inner flexures 7. The restoring force $F_{ri}$ created by the inner flexures 7 is given by $$F_{ri} = k_i x_f = n_{fi} \frac{Etw_i}{l_i^3} x_f.$$

The sensor probe 4 is attached by micro assembly to the inner movable body in a rigid way such as epoxy glue. Also the sensor probe 4 can be made of silicon and fabricated with the same fabrication process as the rest of the sensor. To measure the force F that is applied to the sensor probe 4 during operation, a differential position sensing capacitive comb drive 9 is used that is measuring the displacement $x_f$ between the inner movable body 3 and the outer movable body 2. The capacitance change $C_F$ is given by $$C_F = \varepsilon A_f \left( \frac{1}{d_{f1} - x_f} - \frac{1}{d_{f2} + x_f} \right) - \varepsilon A_f \left( \frac{1}{d_{f1} + x_f} - \frac{1}{d_{f2} - x_f} \right)$$

where $d_{f1}$ is the air gap between the capacitor plates and $d_{f2}$ is the spacing between the capacitor electrode pairs in a differential comb drive pair configuration (the buildup of differential comb drives are described in more detail in [4]), $$\varepsilon = 8.85 \times 10^{-12} C^2/(Nm^2)$$

is the permittivity of air and $A_f$ is the area of the parallel plate capacitor formed by the comb drive. The force sensor capacitive interface 21 transduces the change of capacitance $C_f$ into an analog or digital output force signal $S_F$.

The sensor probe 4 is electrically insulated from the rest of the sensor to enable testing in aqueous environments (immerse the sensor probe into liquid). This is realized by etching air gaps into the device layer of a silicon-on-insulator (SOI) wafer. Mechanically, the parts are connected by the handle layer that is separated from the device layer by a layer of silicon oxide ($SiO_2$). Electrically, the sensor probe is connected through at least one of the inner flexures 7 and at least one of the outer flexures 5 to the fixed body 1. On the fixed body 1 there is a separate electrical pad for wire-bonding. This allows setting the sensor probe 4 to a defined electrical potential by a connector on the printed circuit board (PCB) or on the chip carrier. Alternatively, the sensor probe 4 can be used as an electrical probe also (in combination to the mechanical testing).

To push the sensor probe 4 against the sample to be tested, a high resolution actuator is required. An electrostatic actuator 6 can be directly integrated into the scanning force sensor 100. The electrostatic actuator 6 is pushing the outer movable body 2 in the x-direction. The outer flexures 5 are creating the restoring force for controlling the position of the sensor probe 4. Alternatively, this scanning motion can also be generated by an electro-thermal actuator 10.

Electrostatic actuation has the advantage that there is no heating of the sensor chip. By using a lateral comb drive configuration a large travel range can be achieved without the risk of the pull-in effect that is limiting the range of transverse comb drive actuators. The electrostatic driving force $f_e$ for a single finger pair is given by $$f_e = \varepsilon \frac{tV^2}{d_a}.$$

For a lateral configuration, where $\varepsilon = 8.85 \times 10^{-12} C^2/Nm^2$) is the permittivity of air, V is the driving voltage, $d_a$, is the distance between the plates, and t is the thickness of the wafer (thickness in z-direction). The driving voltage is supplied by a voltage supply 20 that is controlled by a computer. For a set of $n_a$ capacitors, the total driving force $F_e$ is given by $$F_e = n_a \varepsilon \frac{tV^2}{d_a}.$$

To electrically insulate the actuator from the rest of the sensor it is separated by an air gap. This is realized by etching air gaps into the device layer of a silicon-on-insulator (SOI) wafer. Mechanically, the parts are connected by the handle layer that is separated from the device layer by a layer of silicon oxide ($SiO_2$).

Figure 2:
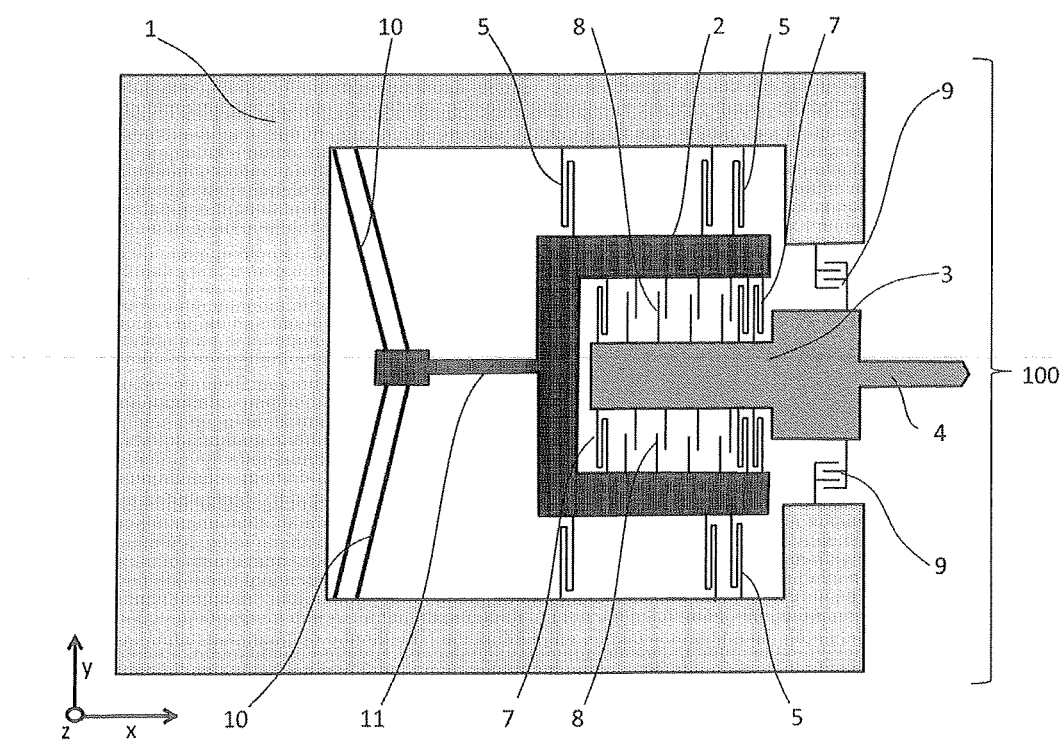
FIG. 2 is an illustration of the scanning MEMS force sensor chip with electro-thermal actuation.
Figure 3:
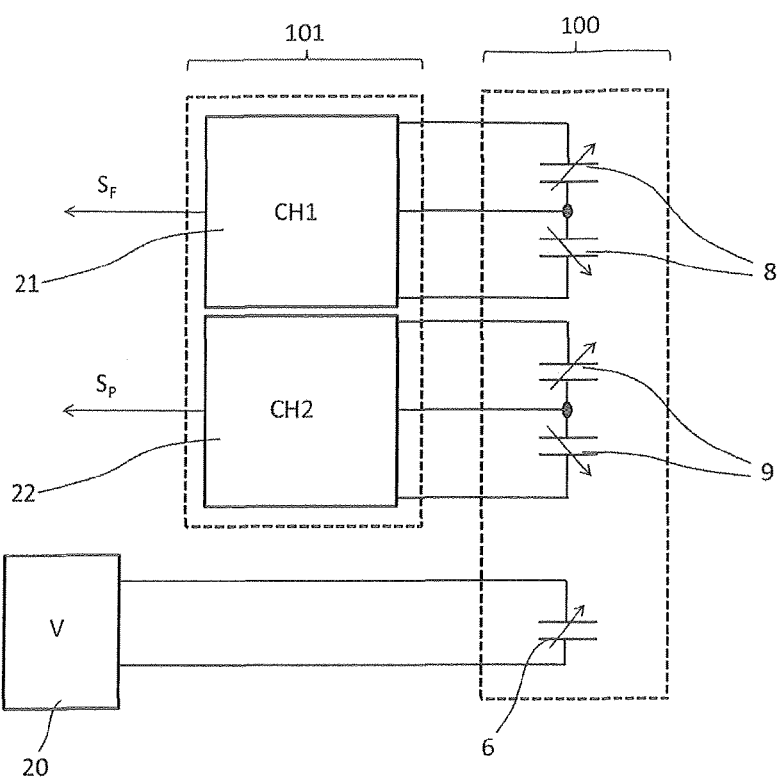
FIG. 3 is an electrical schematic of an electrostatic scanning force sensor and interface electronics.
Figure 4:
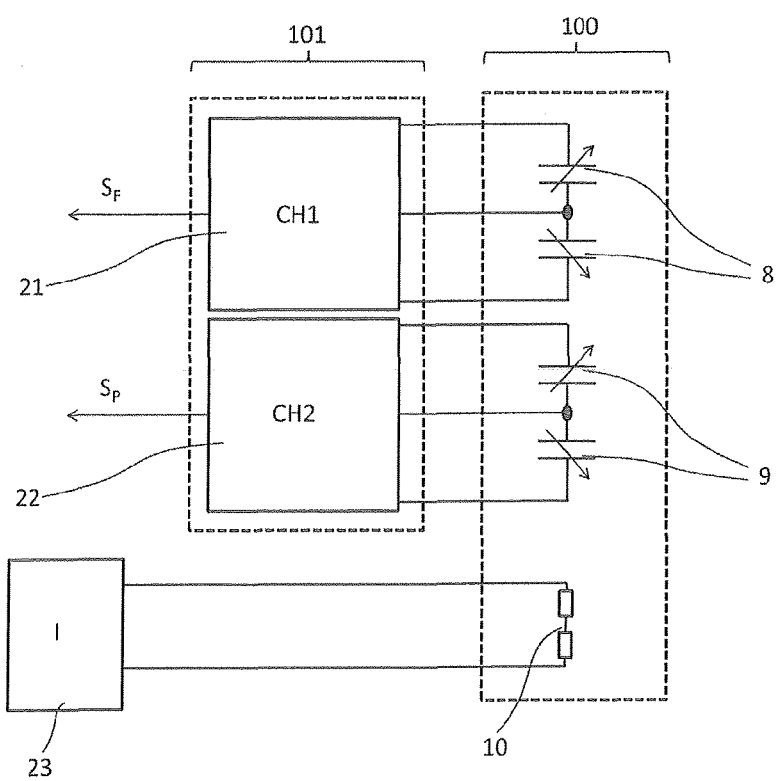
FIG. 4 is an electrical schematic of an electro-thermal scanning force sensor and the interface electronics.

Electro-thermal actuators 10 have the advantage of a simple and mechanically stiff structure. Also, relatively large actuation forces are created during thermal expansion. To increase the actuation range one or multiple v-shaped heater designs are chosen that expand if an electrical current is put across them. A sensor configuration with a multi-beam v-shaped electro-thermal actuator 10 is shown in FIG. 2.

Electro-thermal actuators 10 have the disadvantage to heat up the scanning force sensor 100. However, by integrating a cooling rip 11 which connects the outer movable body 2 to the electro-thermal actuator 10, the heating of the rest of the scanning force sensor 100, but especially the comb drives can be reduced (thermal expansion may lead to unwanted sensor drift). A computer controlled current supply 23 is used to control the electro-thermal actuator 10.

For micro-mechanical and nano-mechanical testing it is important to have two independent output signals: $S_F$ for the force and $S_P$ for the position of the sensor probe 4. A multi-channel capacitive interface electronics 101 is required containing a force sensor capacitive interface 21 and a position sensor capacitive interface 22. Multi-channel capacitive interface electronics 101 as integrated circuits (ICs) are commercially available.

The position of the sensor probe 4 is measured by a differential position sensing capacitive comb drive 9 which is measuring the relative deflection between the fixed body 1 and the inner movable body 3 which is connected to the sensor probe 4. With this configuration, the deformation or indentation of the sample to be tested can be measured when the sensor probe tip 4 is pushing against the sample. The position measurement works independently from the actuation (scanner) and the force sensing. No mathematical models are used to compute the position or the force.

For the position measurement, a lateral differential comb drive pair is used. The differential change of capacitance $C_P$ is given by
a)

$$C_P = \varepsilon A_P \left( \frac{1}{d_{p1} - x_p} - \frac{1}{d_{p2} + x_p} \right) - \varepsilon A_P \left( \frac{1}{d_{p1} + x_p} - \frac{1}{d_{p2} - x_p} \right)$$

where $d_{p1}$ is the air gap between the capacitor plates and $d_{p2}$ is the spacing between the capacitor electrode pairs in a differential comb drive pair configuration (the buildup of differential comb drives are described in more detail in [4]). The position sensor capacitive interface 22 transduces the change of capacitance $C_P$ into an analog or digital output force signal $S_P$.

Figure 5:
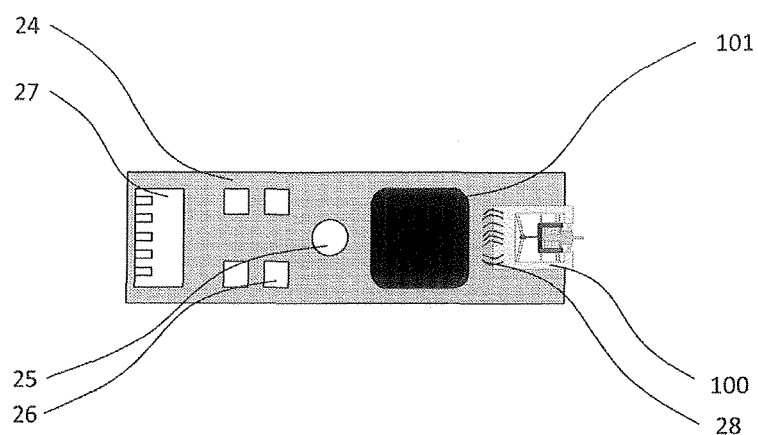
FIG. 5 is a block diagram of electro-thermal scanning force sensor and the interface electronics.

For interfacing the scanning force sensor 100 chip it is mounted on a printed circuit board (PCB) 24 or a chip carrier as illustrated in FIG. 5. Electrical contact is made by wire-bonding or a chip-flip reflow process. All electrical bonding pads of the scanning force sensor are located on the fixed body (the outer movable part and the inner movable part must not be fixed on the chip carrier or PCB). The sensor probe is overhanging the chip carrier or PCB to enable access to the sample.

The scanning force sensor 100 and the multi-channel capacitive interface electronics create two independent output signals $S_F$ and $S_P$. Therefore, multi-channel capacitive interface electronics 101 with at least two channels are required. To reduce the effect of parasitic capacitance, it is advisable to locate the multi-channel capacitive interface electronics 101 directly on the PCB 24 next to the scanning force sensor 100. Electrical pads 26 on the PCB 24 will enable the programming of the memory of interface integrated circuits (ICs). A mounting hole enables the fixation of the PCB 24 or chip carrier on a positioning unit which is used for the sensor-to-sample alignment.

The following is a summary list of reference numerals and the corresponding structure used in the above description of the invention:
1 Fixed body
2 Outer movable body
3 Inner movable body
4 Sensor probe
5 Outer flexure
6 Electrostatic microactuator
7 Inner flexure
8 Force sensing capacitive comb drive
9 Position sensing capacitive comb drive
10 Electro-thermal microactuator
11 Cooling rip
20 Voltage supply
21 Force sensor capacitive interface
22 Position sensor capacitive interface
23 Current supply
24 Printed circuit board (PCB)
25 Mounting hole
26 Electrical pads
27 Connector
28 Wire-bonds
100 Scanning force sensor
101 Multi-channel capacitive interface electronics
IC Integrated Circuit
PCB Printed Circuit Board
SOI Silicon On Insulator
CH1 Channel 1
CH2 Channel 2

REFERENCES

[1] A microelectromechanical load sensor for in situ electron and x-ray microscopy tensile testing of nanostructures, Y. Zhu, N. Moldovan, H. D. Espinosa, App. Phys. Lett. 18, 13 (2005).

[2] A novel MEMS nano tribometer for dynamic testing in-situ in SEM and TEM, A. V. Desai and M. A. Hague, Trib. Lett. 18, 13 (2005).

[3] A micromachined nanoidentation force sensor, A Nafari, A. Danilov, H. Rodjegard, P. Enoksson, and H. Olin, Sens. Actuator A 123-124,44 (2005).

[4] A bulk micro fabricated multi-axis capacitive cellular force sensor using transverse comb drives, Y. Sun, B. J. Nelson, D. P. Potasek, E. Enikov, J. Micromech. Microeng. 12, 832 (2002).

[5] MEMS Nanoindenter, Enoksson et al., U.S. Pat. No. 7,654,159.

[6] A Novel Dual-Axis Electrostatic Microactuation System for Micromanipulation, Sun et al, Proceedings of the 2002, IEEWRSJ Intl. Conference on Intelligent Robots and Systems EPFL, Lausanne, Switzerland October 2002.

[7] Micromachined Comb Drive for Quantitative Nanoindentation, Oh et al., U.S. Pat. No. 8,161,803 B2.

[8] 2-D MEMS tribometer with comb drives, Oh et al., US 2011/0265559 A1.

[9] Actuable capacitive transducer for quantitative nanoindentation combined with transmission electron microscopy, Warren et al, US 0070180924A1.

The invention claimed is:

1. A micro-electro-mechanical system scanning force sensor for a simultaneous measurement of a force applied to a sample and a deformation of the sample, comprising:
   a position sensing capacitive comb drive for measuring the deformation of the sample;
   a force sensing capacitive comb drive for measuring the force applied to the sample, said position sensing capacitive comb drive and said force sensing capacitive comb drive enabling simultaneous force and deformation sensing; and
   a micro-actuator for applying a mechanical load onto the sample, said micro-actuator selected from the group consisting of an electrostatic micro-actuator and an electro-thermal micro-actuator;
   a fixed body;
   outer flexures;
   inner flexures;
   an outer movable body suspended by multiple ones of said outer flexures, said outer flexures connected between said outer movable body and said fixed body; and
   an inner movable body suspended by multiple ones of said inner flexures, said inner flexures connected between said inner movable body and said outer movable body.

2. The scanning force sensor according to claim 1, further comprising a sensor probe connected to said inner movable body.

3. The scanning force sensor according to claim 1, further comprising:
   a force sensor capacitive interface; and
   a position sensor capacitive interface, said force sensing capacitive comb drive and said position sensing comb drive generate two independent capacitive output signals that are interfaced by said force sensor capacitive interface and said position sensor capacitive interface.

4. The scanning force sensor according to claim 1, wherein said electrostatic micro-actuator or said electro-thermal micro-actuator are mechanically connected to said outer movable body to generate a relative motion between said outer movable body and said fixed body.

5. The scanning force sensor according to claim 4, wherein said position sensing capacitive comb drive is measuring a relative motion between said inner movable body and said fixed body.

6. The scanning force sensor according to claim 1, wherein said force sensing capacitive comb drive is measuring a relative motion between said inner movable body and said outer movable body.

7. The scanning force sensor according to claim 1, further comprising a cooling rip, said electro-thermal micro-actuator is connected to said outer movable body by said cooling rip.

8. The scanning force sensor according to claim 1, wherein said electro-thermal micro-actuator has a v-shaped geometrical amplification mechanism to increase a scanning range of the scanning force sensor.

9. The scanning force sensor according to claim 1, further comprising:
   a support selected from the group consisting of a printed circuit board and a chip carrier; and
   a sensor probe electrically connected to said printed circuit board or to said chip carrier through at least one of said outer flexures and at least one of said inner flexures.

10. The scanning force sensor according to claim 9, further comprising a multi-channel capacitive interface electronics integrated circuit; and
    wherein components of the scanning force sensor are mounted on said printed circuit board or on said chip carrier including said multi-channel capacitive interface electronics integrated circuit.

* * * * *